United States Patent
Horiike et al.

(10) Patent No.: US 9,513,257 B2
(45) Date of Patent: Dec. 6, 2016

(54) DISCHARGE IONIZATION CURRENT DETECTOR AND METHOD FOR AGING TREATMENT OF THE SAME

(75) Inventors: Shigeyoshi Horiike, Kyoto (JP); Kei Shinada, Kyoto (JP); Takahiro Nishimoto, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 166 days.

(21) Appl. No.: 14/382,600

(22) PCT Filed: Mar. 15, 2012

(86) PCT No.: PCT/JP2012/056674
§ 371 (c)(1),
(2), (4) Date: Oct. 17, 2014

(87) PCT Pub. No.: WO2013/136482
PCT Pub. Date: Sep. 19, 2013

(65) Prior Publication Data
US 2015/0054521 A1 Feb. 26, 2015

(51) Int. Cl.
*G01N 27/62* (2006.01)
*G01N 27/68* (2006.01)
*G01N 27/70* (2006.01)
*G01N 30/64* (2006.01)

(52) U.S. Cl.
CPC .............. *G01N 27/68* (2013.01); *G01N 27/70* (2013.01); *G01N 30/64* (2013.01); *G01N 2030/647* (2013.01)

(58) Field of Classification Search
CPC ........ G01N 27/68; G01N 27/70; G01N 27/62; G01N 2030/642

USPC ......................... 324/464, 465, 466, 467, 468
See application file for complete search history.

(56) References Cited

U.S. PATENT DOCUMENTS

| | | | |
|---|---|---|---|
| 5,394,092 A * | 2/1995 | Wentworth | G01N 27/70 324/455 |
| 5,892,364 A | 4/1999 | Monagle | |
| 7,091,481 B2 * | 8/2006 | Miller | H05H 1/24 250/286 |
| 7,862,736 B2 * | 1/2011 | Nakayama | B08B 7/0035 156/345.24 |
| 8,349,125 B2 * | 1/2013 | Vane | B08B 7/0035 156/345.43 |

(Continued)

FOREIGN PATENT DOCUMENTS

| | | |
|---|---|---|
| JP | 2011-158357 A | 8/2011 |
| JP | 2012-008088 A | 1/2012 |
| WO | 2009/119050 A1 | 10/2009 |

OTHER PUBLICATIONS

International Search Report dated Jun. 19, 2012, issued in corresponding application No. PCT/JP2012/056674.

*Primary Examiner* — Tung X Nguyen
*Assistant Examiner* — Dominic Hawkins
(74) *Attorney, Agent, or Firm* — Westerman, Hattori, Daniels & Adrian, LLP

(57) ABSTRACT

An aging treatment is performed by using cleaning gas obtained by mixing inert gas, as an impurity, to plasma gas. Plasma generation by dielectric-barrier discharge is performed until a predetermined period of time has elapsed by applying high AC voltage to an electrode while supplying the cleaning gas to a dielectric tube from a gas inlet.

11 Claims, 6 Drawing Sheets

(56) References Cited

U.S. PATENT DOCUMENTS

| | | | |
|---|---|---|---|
| 8,421,470 B2* | 4/2013 | Kitano | G01N 27/68 |
| | | | 324/464 |
| 8,916,056 B2* | 12/2014 | Koo | H01J 37/32422 |
| | | | 134/1.1 |
| 2005/0121607 A1* | 6/2005 | Miller | H05H 1/24 |
| | | | 250/287 |
| 2008/0233723 A1* | 9/2008 | Okumura | H01J 37/32091 |
| | | | 438/513 |
| 2011/0018546 A1 | 1/2011 | Kitano et al. | |
| 2011/0187379 A1* | 8/2011 | Shinada | G01N 27/70 |
| | | | 324/464 |
| 2011/0316551 A1 | 12/2011 | Shinada et al. | |

* cited by examiner

DISCHARGE IONIZATION CURRENT DETECTOR AND METHOD FOR AGING TREATMENT OF THE SAME

TECHNICAL FIELD

The present invention relates to a discharge ionization current detector adopting a method for ionizing a sample by plasma that is generated by dielectric-barrier discharge, and a method for an aging treatment of the same.

BACKGROUND ART

As a trace gas detector for a gas chromatograph, detectors adopting various methods, such as a TCD (Thermal Conductive Detector) and an ECD (Electric Capture Detector), are being proposed and put to practical use, and a detector that is currently most generally used is an FID (Flame Ionization Detector). The FID achieves a wide dynamic range (about six figures) by ionizing sample gas by a hydrogen flame and measuring the ionization current thereof. However, there is a disadvantage that it is not suitable for detection of inorganic gas and fire-retardant gas. On the other hand, there is a discharge ionization current detector which performs detection by generating an excited species of inert gas, such as He, $N_2$, Ar, Ne or Xe, by plasma that is generated by high-voltage discharge and by ionizing a sample. A PDD (Pulsed Discharge Detector), which is one of such discharge ionization current detectors, generates plasma by causing spark discharge by application of a pulsed high voltage. A method that uses plasma does not need hydrogen and, generally, the ionization efficiency of a sample is increased compared to the FID and the sensitivity is high, having sensitivity for inorganic gas and fire-retardant gas, but there is a disadvantage that the dynamic range is narrow compared to the FID.

Also, in contrast to the PDD, there is a discharge ionization current detector which adopts a method for generating plasma by dielectric-barrier discharge (Patent Document 1). With the dielectric-barrier discharge, since the surface of a discharge electrode is covered with a dielectric material, there is not much emission of thermal electrons, secondary electrons and the like that occur in the case of generating discharge between metal electrodes, and the stability of plasma generation is high. Also, a discharge current is suppressed by the dielectric material, and thus, there are characteristics that deterioration of electrodes and heat generation at electrodes may be suppressed, and that the durability is high.

PRIOR ART DOCUMENTS

Patent Documents

Patent Document 1: Japanese Patent Laid-open Publication No. 2011-158357

SUMMARY OF THE INVENTION

Problems to be Solved by the Invention

According to a discharge ionization current detector, normally, a plasma generation section for generating plasma by discharge and a sample ionization detection section for ionizing and detecting a sample are spatially connected to each other, and plasma gas flowing through the plasma generation section flows into the sample ionization detection section. Then, the discharge ionization current detector ionizes the impurities contained in the gas flowing through the plasma generation section, and thus, there is a disadvantage that ionized impurities are detected and the background of the detection signal is increased. Accordingly, in the case where an extremely low lower limit of detection (high sensitivity) is required, plasma gas such as helium gas is refined and concentration of impurities is reduced to the unit of ppb.

With a discharge ionization current detector that uses dielectric-barrier discharge, quartz is often used as the dielectric material for covering the discharge electrode. Quartz has adsorption with respect to water, and adsorbed water will be present on the surface of quartz exposed to air. Accordingly, if measurement is performed immediately after installation of the discharge ionization current detector, the adsorbed water on the surface of quartz covering the discharge electrode is ionized and detected, and the background of the detection signal will be increased. Thus, the adsorbed water on the quartz is removed by applying, after installation of the detector, a baking treatment of heating the detector at a temperature higher than the temperature to be used for several hours to several days, or by applying, after installation of the detector, at the same time as the baking treatment or after the baking treatment, an aging treatment of performing plasma generation same as at the time of normal measurement at a plasma generation section, and the background of the detection signal is reduced.

The background of a detection signal may be reduced to a certain extent by applying the baking treatment or the aging treatment mentioned above, but to realize a higher detection sensitivity, the background of the detection signal is desirably further reduced.

Accordingly, the present invention has its aim to highly efficiently reduce the background of a detection signal of a discharge ionization current detector that uses dielectric-barrier discharge.

Solutions to the Problems

The present inventors have found that the efficiency of reducing the background of a detection signal is greater in the case of performing the aging treatment by using gas obtained by mixing inert gas with greater atomic weight than plasma gas in the plasma gas which is to flow through a plasma generation section than in the case of performing the aging treatment by using the plasma gas. This is considered to be due to suppression of initial gas discharge by inert gas with greater atomic weight than plasma gas receiving energy from the plasma gas by being mixed in the plasma gas, the wall surface of a dielectric barrier being sputtered and desorption of adsorbed molecules being promoted.

The present invention has been made in view of the above knowledge. That is, a method for aging treatment of the present invention is a method for aging treatment of a discharge ionization current detector including a plasma generation section that is configured of a dielectric tube and a plurality of electrodes attached on an outer circumference of the dielectric tube, the plasma generation section continuously generating dielectric-barrier discharge inside the dielectric tube by applying high AC voltage to the electrodes while causing plasma gas to flow through the dielectric tube, a sample ionization section that is connected to a downstream end of the dielectric tube and that ionizes components in sample gas by light at a time of discharge generation at the plasma generation section, and an ion detection section that detects a sample component ionized by the sample ionization section, the method including continuously generating the dielectric-barrier discharge over a predetermined period of time by the plasma generation section while supplying, as cleaning gas, mixed gas obtained by mixing inert gas with greater atomic weight than the plasma gas in the plasma gas, to the dielectric tube.

A discharge ionization current detector of the present invention is configured to enable the aging treatment method described above to be easily performed. That is, a discharge ionization current detector of the present invention includes a plasma generation section that is configured of a dielectric tube and a plurality of electrodes attached on an outer circumference of the dielectric tube, the plasma generation section continuously generating dielectric-barrier discharge inside the dielectric tube by applying high AC voltage to the electrodes while causing plasma gas to flow through the dielectric tube, a sample ionization section that is connected to a downstream end of the dielectric tube and that ionizes components in sample gas by light at a time of discharge generation at the plasma generation section, an ion detection section that detects a sample component ionized by the sample ionization section, a plasma gas supply section for supplying the plasma gas, a cleaning gas supply section for supplying, as cleaning gas, mixed gas obtained by mixing inert gas with greater atomic weight than the plasma gas in the plasma gas, and a supply gas switching mechanism that connects the plasma gas supply section or the cleaning gas supply section to the dielectric tube and switches between gases.

Effects of the Invention

The aging treatment method of the present invention causes dielectric-barrier discharge to be continuously generated by a plasma generation section while supplying, as cleaning gas, mixed gas obtained by mixing inert gas with greater atomic weight than plasma gas in the plasma gas, and thus, the efficiency of removal of impurities on the surface of a discharge electrode is increased, and the background of a detection signal may be highly efficiently reduced. Thus, the background of a detection signal can be reduced to a level that cannot be reached by a conventional aging treatment, with about the same processing time as the conventional aging treatment, and the detection sensitivity of a detector may be increased.

EMBODIMENTS OF THE INVENTION

Inert gas of a method for an aging treatment and a discharge ionization current detector of the present invention refers to gas that has no reactivity to a sample component.

Further, an example of plasma gas of the method for an aging treatment and the discharge ionization current detector of the present invention is helium, and an example of the inert gas in this case is nitrogen or argon, for example. Of all the inert gases, helium has the smallest atomic weight, and voltage necessary for generating plasma at a plasma generation section is the lowest.

When the atomic weight of gas flowing through the plasma generation section becomes greater, voltage necessary for generating plasma at the plasma generation section becomes higher. Accordingly, if the proportion of the inert gas with greater atomic weight than plasma gas is made greater than the proportion of the plasma gas, plasma is less likely to be generated at the plasma generation section, and as a result, the efficiency of removal of impurities by a dielectric tube is reduced.

Accordingly, in the aging method of the present invention, the proportion of the inert gas in cleaning gas is desirably made smaller than the proportion of the plasma gas.

Figure 1:
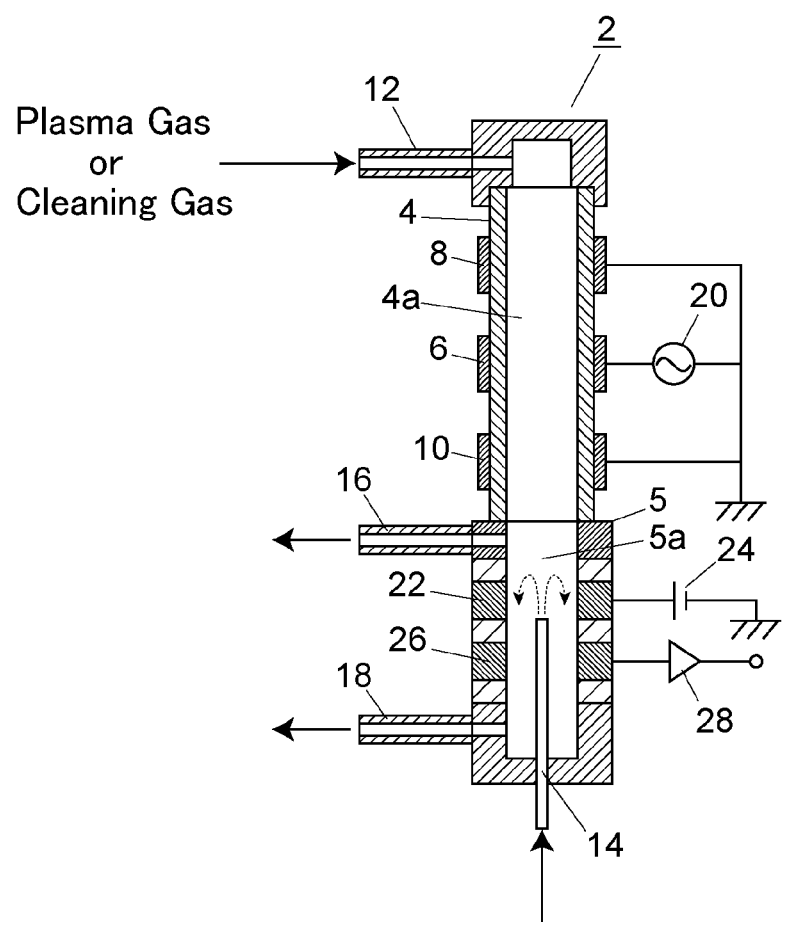
FIG. 1 is a cross-sectional view of a schematic configuration for describing an example of the configuration of a discharge ionization current detector.

First, an example of the configuration of a discharge ionization current detector that uses dielectric-barrier discharge will be described with reference to FIG. 1.

A discharge ionization current detector 2 includes a plasma generation section, a sample ionization section, and a sample ion detection section. The plasma generation section is configured of a dielectric tube 4 formed of dielectric material such as quartz or sapphire, for example, and ring electrodes 6, 8 and 10 attached at three positions separate from one another on the outer circumference of the dielectric tube 4. High AC voltage is to be applied to the electrode 6 by an AC power supply 20. The two electrodes 8 and 10 arranged on the opposite sides of the electrode 6 are grounded.

A gas inlet 12 is provided at one end of the dielectric tube 4. Mixed gas of helium gas (plasma gas) and argon gas (inert gas) mixed in the helium gas as an impurity is supplied from the gas inlet 12 as cleaning gas when needed. Helium gas is supplied from the gas inlet 12 at the time of analysis of a sample, and cleaning gas is supplied from the gas inlet 12 at the time of an aging treatment described later. The plasma gas or the cleaning gas supplied from the gas inlet 12 is discharged from a gas outlet 16 or 18 described later through a passage 4a in the dielectric tube 4.

When high AC voltage is applied to the electrode 6 in a state where the plasma gas or the cleaning gas is being supplied inside the dielectric tube 4, dielectric-barrier discharge occurs between the electrode 6 and the electrode 8 and between the electrode 6 and the electrode 10, and the plasma gas or the cleaning gas flowing through the passage 4a in the dielectric tube 4 is excited by the discharge, thereby generating plasma.

One end of a tube 5 forming the sample ionization section and the sample ion detection section is connected to the downstream side of the dielectric tube 4. A capillary 14 is inserted in the other end of the tube 5. A tip end of the capillary 14 is arranged facing the downstream end of the dielectric tube 4, in a space 5a on the side of the one end rather than a charge collecting electrode 26 described later. Although not shown, a base end of the capillary 14 communicates with an analytical column of a gas chromatograph, and at the time of analysis of a sample, sample gas which has passed through the analytical column is injected toward the downstream end of the dielectric tube 4 from the tip end of the capillary 14.

The tube 5 includes, from the side of the one end, a bias electrode 22 and a charge collecting electrode 26. The bias electrode 22 and the charge collecting electrode 26 are both ring electrodes and both face the inner space 5a. DC voltage is to be applied to the bias electrode 22 by a DC power supply 24. Sample gas injected from the tip end of the capillary 14 into the space 5a in the tube 5 is ionized by excitation light emitted at the time of generation of dielectric-barrier discharge at the plasma generation section. Potential is applied to the ionized sample by the bias electrode 22, and the sample is collected by the charge collecting electrode 26 and is outputted as a current signal after being amplified by a current amplifier 28.

The gas outlet 16 is provided on a side wall on the side of the one end of the tube 5, and the gas outlet 18 is provided on a side wall on the side of the other end of the tube 5. The gas outlet 16 is provided on the side more to the one end than the bias electrode 22, and the gas outlet 18 is provided on the side more to the other end than the charge collecting electrode 26. At the time of analysis of a sample, a part of plasma gas from the dielectric tube 4 is discharged from the gas outlet 16, and the rest of the plasma gas from the dielectric tube 4 and the sample gas pushed back by the plasma gas are discharged from the gas outlet 18.

Figure 2:
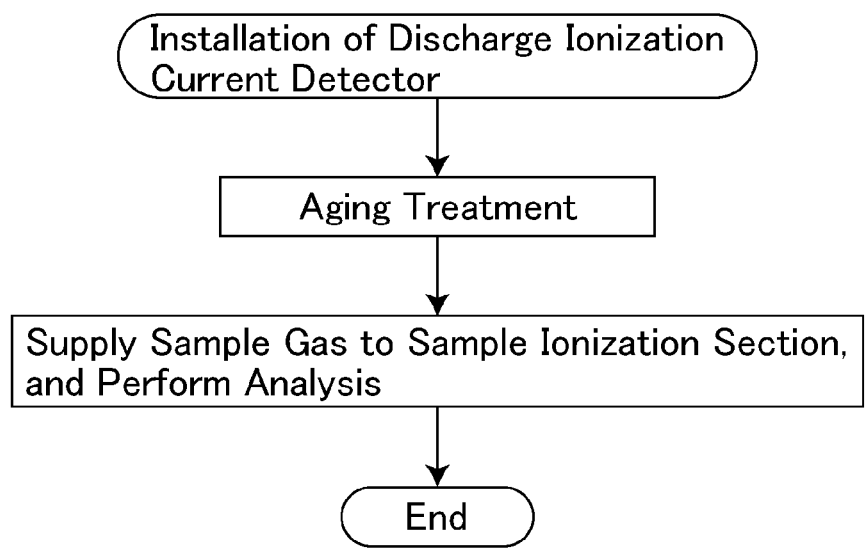
FIG. 2 is a flow chart for describing the work flow after installation of the discharge ionization current detector.

After this discharge ionization current detector 2 has been installed as the detector of the gas chromatograph, an aging treatment for reducing the background of a detection signal by removing impurities such as water attached to the dielectric tube 4 is performed as shown in FIG. 2. Then, when the aging treatment is completed, sample gas is supplied to the space 5a in the tube 5, and analysis of the sample is started.

Figure 3:
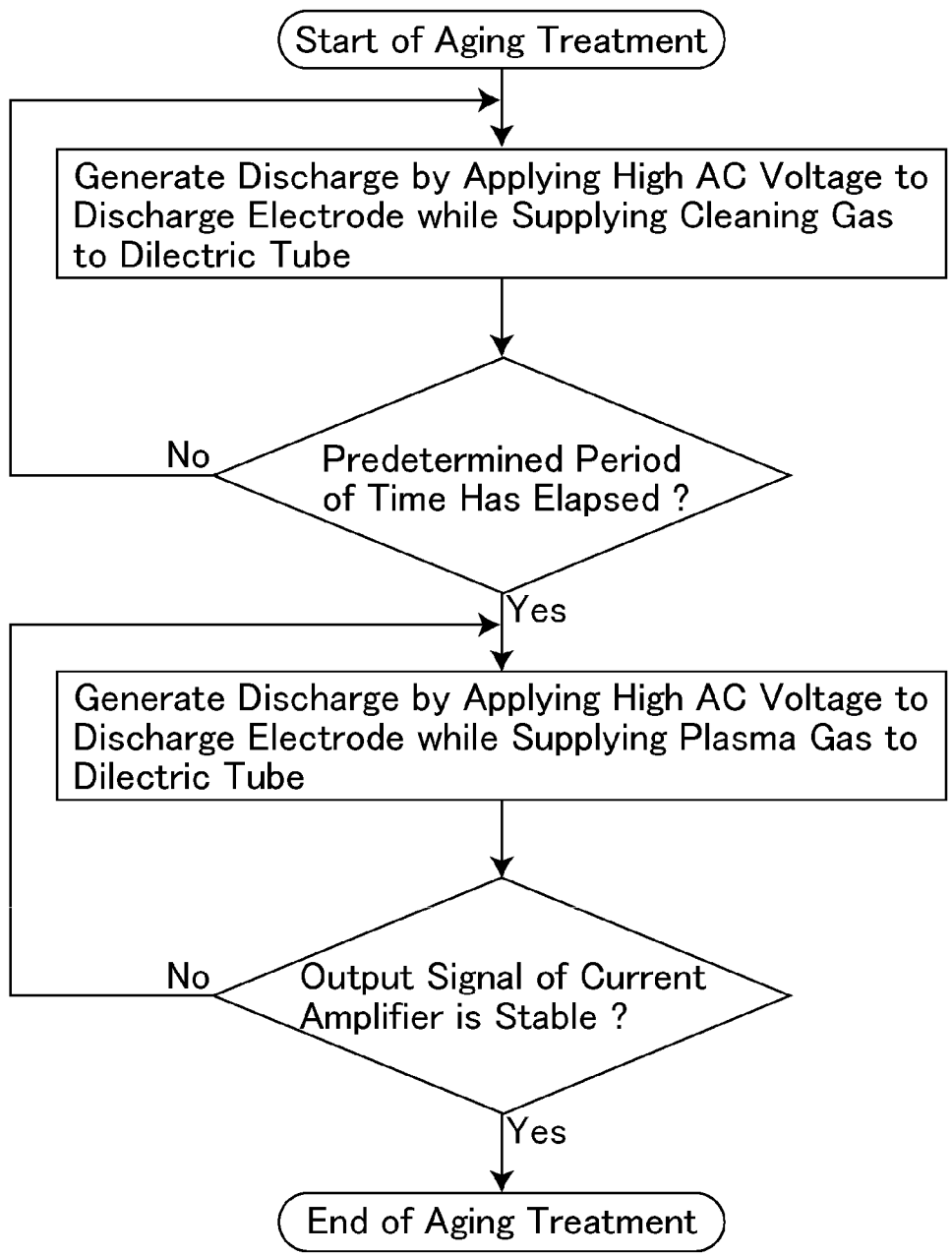
FIG. 3 is a flow chart for describing an example of an aging treatment.

The aging treatment for reducing the background of a detection signal will be described with reference to the flow chart of FIG. 3.

The aging treatment is performed by using cleaning gas which is obtained by mixing inert gas as an impurity in the plasma gas. In the case where helium gas is used as the plasma gas, nitrogen gas or argon gas may be used as the inert gas. In the case where argon gas is used as the inert gas, the cleaning gas may be prepared in such a way that the concentration of the argon gas is, for example, 1000 ppm to 20%. Particularly, if the concentration of the argon gas is about 1 to 2%, the S/N of the output signal of the current amplifier 28 will be good, and observation of the progress of the aging treatment will be facilitated.

Additionally, as the combination of the plasma gas and the inert gas, there may be cited a case where the plasma gas is helium and the inert gas is argon or xenon, a case where the plasma gas is neon and the inert gas is argon or xenon, and a case where the plasma gas is argon and the inert gas is xenon. A combination which is particularly desirable is the combination where the plasma gas is helium and the inert gas is argon.

Plasma generation by dielectric-barrier discharge is performed for a predetermined period of time, such as several hours to one day, by applying high AC voltage to the electrode 6 while supplying the cleaning gas to the dielectric tube 4 from the gas inlet 12. In the case where the inner diameter of the dielectric tube 4 is about 2 to 3 mm, the flow rate of the cleaning gas may be between 20 and 100 ccm, for example, about 40 ccm. In this aging treatment, the high AC voltage to be applied to the electrode 6 may be of the same amplitude (magnitude) and frequency as those of the high AC voltage that is used at the time of measurement of the sample.

Then, the gas to be supplied from the gas inlet 12 is switched to the plasma gas, and generation of plasma by discharge is continued until the output signal of the current amplifier 28 is stable by continuing application of high AC voltage to the electrode 6, and all of the cleaning gas in dielectric tube 4 and the tube 5 is replaced by the plasma gas. The aging treatment of the detector 2 is thereby ended.

Figure 4:
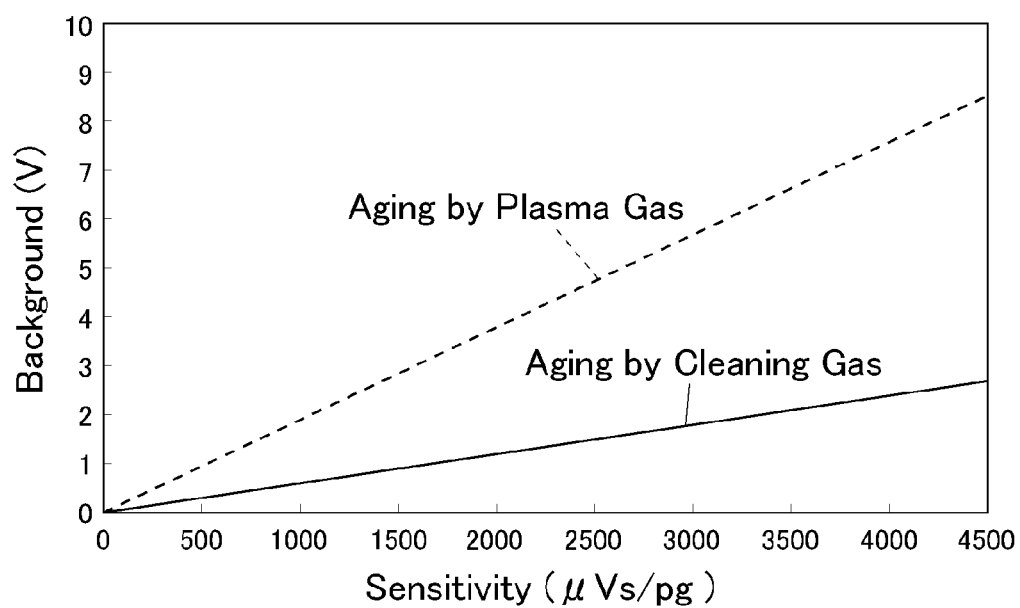
FIG. 4 is a graph showing the background of a detection signal of a detector on which an aging treatment by plasma gas has been applied and the background of a detection signal of a detector on which an aging treatment by cleaning gas has been applied.

FIG. 4 is a graph showing data (dotted line) of measurement of the background of a detection signal of a detector on which an aging treatment by plasma gas has been applied and data (solid line) of measurement of the background of a detection signal of a detector on which an aging treatment by cleaning gas prepared by mixing argon in helium by the amount of 2% has been applied. The dielectric tubes 4 of the detectors used in the measurement are both quartz tubes where the OH concentration is 5 ppm or less. Also, the processing time of the aging treatment by the plasma gas and the processing time of the aging treatment by the cleaning gas are the same.

The background of a detection signal of the discharge ionization current detector tends in increase in proportion to the setting sensitivity, but the background of the detector on which the aging treatment by the cleaning gas has been applied is reduced to half or less than the background of the detector on which the aging treatment by the plasma gas has been applied. Accordingly, it can be seen that, by applying the aging treatment by using the cleaning gas, the background can be reduced to a level that cannot be reached by a conventional aging treatment.

Figure 5:
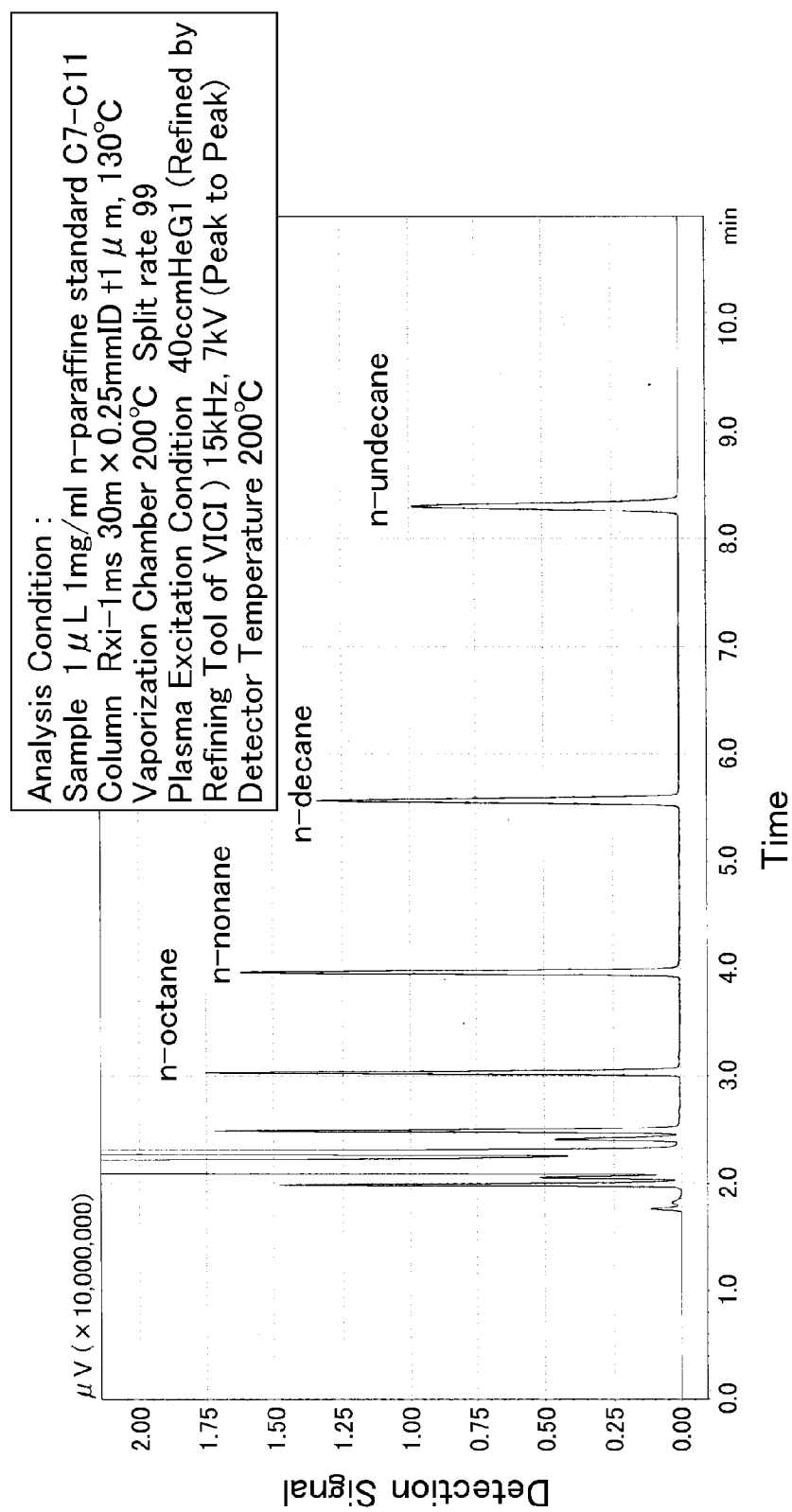
FIG. 5 is a chromatogram of dodecane measured by a detector on which an aging treatment has been applied by cleaning gas.

FIG. 5 is data of a chromatogram of 10 ng of dodecane measured by a detector on which an aging treatment has been applied by using the cleaning gas. As shown in the drawing, with a detector on which an aging treatment by the cleaning gas has been applied, high S/N is realized for the detection signal, and MDQ (logical minimum detectable quantity) reaches 0.22 pgC/sec. On the other hand, with a detector on which a conventional aging treatment by plasma gas has been applied, the limit of MDQ is about 0.60 pgC/sec. That is, by applying the aging treatment by the cleaning gas, MDQ which was not realized by the conventional aging treatment can be realized. Additionally, MDQ may be obtained by the following expression by taking the background noise of a detection signal as N ($\mu$V) and the mass sensitivity of a standard sample (in this case, n-dodecane) as S ($\mu$V·sec/pg).

$$MDQ=2N/S$$

Figure 6:
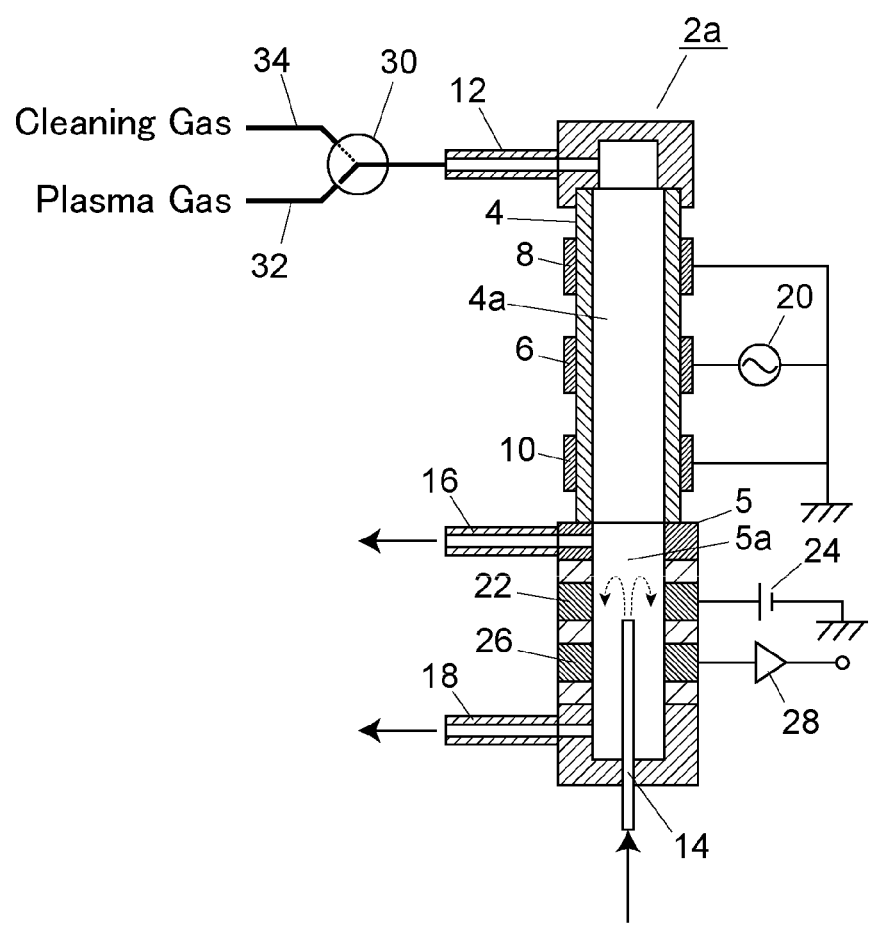
FIG. 6 is a cross-sectional view of a schematic configuration showing an embodiment of the discharge ionization current detector.

An example of a discharge ionization current detector configured in such a way as to enable easy application of the aging treatment by the cleaning gas described in the embodiment above will be described with reference to FIG. 6. Additionally, the basic configuration of the discharge ionization current detector is the same as that in FIG. 1, and description of the overlapping structural components will be omitted.

A plasma gas supply passage 32 and a cleaning gas supply passage 34 are connected to a passage communicating with a gas inlet 12 of a dielectric tube 4 of a discharge ionization current detector 2a via a switching valve 30. The switching valve 30 is to connect the passage of one of the plasma gas supply passage 32 and the cleaning gas supply passage 34 to the gas inlet 12 of the dielectric tube 4. The plasma gas supply passage 32 is a passage for supplying helium gas (plasma gas) from a helium gas cylinder via a refining tool.

The cleaning gas supply passage 34 is a passage for supplying cleaning gas prepared by mixing inert gas such as argon gas in helium gas.

According to this configuration, the gas to be supplied from the gas inlet 12 may be switched between plasma gas and cleaning gas simply by switching of the switching valve 30, and an analyst may easily perform the aging treatment by cleaning gas. The switching valve 30 may be manually switched by an analyst as necessary, or a control section of a device may automatically switch the switching valve 30 when the analyst performs input in the device to perform analysis or the aging treatment.

DESCRIPTION OF REFERENCE SIGNS

2: Discharge ionization current detector
4: Dielectric tube
6, 8, 10: Discharge electrode
12: Gas inlet
14: Capillary (for introducing sample gas)
16, 18: Gas outlet
20: High-voltage AC power supply
22: Bias electrode
24: DC power supply
26: Charge collecting electrode
28: Current amplifier
30: Switching valve
32: Plasma gas supply passage
34: Cleaning gas supply passage

What is claimed is:

1. A method for aging treatment of a discharge ionization current detector including: a plasma generation section that is configured of a dielectric tube and a plurality of electrodes attached on an outer circumference of the dielectric tube, the plasma generation section continuously generating dielectric-barrier discharge inside the dielectric tube by applying high AC voltage to the electrodes while causing plasma gas to flow through the dielectric tube; a sample ionization section that is connected to a downstream end of the dielectric tube and that ionizes components in sample gas by light at a time of discharge generation at the plasma generation section; and an ion detection section that detects a sample component ionized by the sample ionization section, the method comprising:
   supplying, as cleaning gas, mixed gas obtained by mixing inert gas with greater atomic weight than the plasma gas in the plasma gas, to the dielectric tube; and
   continuously generating the dielectric-barrier discharge over a predetermined period of time by the plasma generation section while supplying the cleaning gas.

2. The method for aging treatment according to claim 1, wherein the inert gas is gas that has no reactivity to a sample component.

3. The method for aging treatment according to claim 1, wherein the plasma gas is helium, and the inert gas is nitrogen or argon.

4. The method for aging treatment according to claim 1, wherein a proportion of the inert gas in the cleaning gas is smaller than a proportion of the plasma gas.

5. The method for aging treatment according to claim 2, wherein the plasma gas is helium, and the inert gas is nitrogen or argon.

6. The method for aging treatment according to claim 2, wherein a proportion of the inert gas in the cleaning gas is smaller than a proportion of the plasma gas.

7. The method for aging treatment according to claim 3, wherein a proportion of the inert gas in the cleaning gas is smaller than a proportion of the plasma gas.

8. A discharge ionization current detector comprising:
   a plasma generation section that is configured of a dielectric tube and a plurality of electrodes attached on an outer circumference of the dielectric tube, the plasma generation section continuously generating dielectric-barrier discharge inside the dielectric tube by applying high AC voltage to the electrodes while causing plasma gas to flow through the dielectric tube;
   a sample ionization section that is connected to a downstream end of the dielectric tube and that ionizes components in sample gas by light at a time of discharge generation at the plasma generation section;
   an ion detection section that detects a sample component ionized by the sample ionization section;
   a plasma gas supply section for supplying the plasma gas;
   a cleaning gas supply section for supplying, as cleaning gas, mixed gas obtained by mixing inert gas with greater atomic weight than the plasma gas in the plasma gas; and
   a supply gas switching mechanism that connects the plasma gas supply section or the cleaning gas supply section to the dielectric tube and switches between gases.

9. The discharge ionization current detector according to claim 8, wherein the inert gas is gas that has no reactivity to a sample component.

10. The discharge ionization current detector according to claim 8, wherein the plasma gas is helium, and the inert gas is nitrogen or argon.

11. The discharge ionization current detector according to claim 8, wherein a proportion of the inert gas in the cleaning gas is smaller than a proportion of the plasma gas.

* * * * *